United States Patent
Patil et al.

(10) Patent No.: US 12,357,260 B2
(45) Date of Patent: Jul. 15, 2025

(54) MEDICAL IMAGING SYSTEMS AND METHODS WITH AUTO-CORRECTION OF IMAGE QUALITY-BASED ON THE LOG ANALYSIS OF MEDICAL DEVICES

(71) Applicant: KONINKLIJKE PHILIPS N.V., Eindhoven (NL)

(72) Inventors: Meru Adagouda Patil, Bangalore (IN); Ravindra Balasaheb Patil, Bangalore (IN); Vidya Ravi, Bangalore (IN); Sarif Kumar Naik, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 512 days.

(21) Appl. No.: 17/600,806

(22) PCT Filed: Apr. 16, 2020

(86) PCT No.: PCT/EP2020/060667
§ 371 (c)(1),
(2) Date: Oct. 1, 2021

(87) PCT Pub. No.: WO2020/212470
PCT Pub. Date: Oct. 22, 2020

(65) Prior Publication Data
US 2022/0165395 A1    May 26, 2022

Related U.S. Application Data

(60) Provisional application No. 62/834,988, filed on Apr. 17, 2019.

(51) Int. Cl.
*G06T 5/00* (2024.01)
*G06T 5/20* (2006.01)
*G06T 7/00* (2017.01)

(52) U.S. Cl.
CPC ............... *G06T 5/00* (2013.01); *G06T 5/20* (2013.01); *G06T 7/0002* (2013.01);
(Continued)

(58) Field of Classification Search
CPC ............ G06T 5/00; G06T 5/20; G06T 7/0002
See application file for complete search history.

(56) References Cited

U.S. PATENT DOCUMENTS

| 5,600,574 A | 2/1997 | Reitan |
| 2008/0152122 A1* | 6/2008 | Idan ............ H04M 3/5175 379/265.07 |

(Continued)

FOREIGN PATENT DOCUMENTS

WO    2019011765 A1    1/2019

OTHER PUBLICATIONS

International Search Report Dated Aug. 17, 2020 For PCT/EP2020/060667 Filed Apr. 16, 2020.
(Continued)

*Primary Examiner* — Kevin Ky

(57) ABSTRACT

A device for optimizing an image acquisition device (12) includes at least one electronic processor (20) operatively connected to read a machine log (30) of the image acquisition device. A non-transitory computer readable medium (26) stores instructions readable and executable by the at least one electronic processor to perform an image acquisition method (100). The method includes: extracting logged parameters of the image acquisition device from the machine log of the image acquisition device; identifying one or more out-of-range parameters of the image acquisition device from the logged parameters extracted from the machine log of the image acquisition device; automatically tuning one or more electrical or mechanical settings of the image acquisition device on the basis of the one or more out-of-range parameters to transform the image acquisition device into a tuned image acquisition device; and controlling the tuned image acquisition device to acquire one or more images of a patient.

12 Claims, 1 Drawing Sheet

(52) U.S. Cl.
CPC .............. *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/20081* (2013.01); *G06T 2207/20084* (2013.01); *G06T 2207/30004* (2013.01); *G06T 2207/30168* (2013.01)

(56) References Cited

U.S. PATENT DOCUMENTS

| | | | |
|---|---|---|---|
| 2015/0227838 A1 | 8/2015 | Wang | |
| 2016/0120497 A1* | 5/2016 | Nasir | G16Z 99/00 378/207 |
| 2016/0262714 A1 | 9/2016 | Krauss | |
| 2017/0372193 A1 | 12/2017 | Mailhe | |
| 2018/0095653 A1* | 4/2018 | Hasek | G06F 3/04883 |
| 2018/0144243 A1* | 5/2018 | Hsieh | G06F 11/30 |
| 2018/0144465 A1* | 5/2018 | Hsieh | G06N 3/04 |
| 2019/0095678 A1* | 3/2019 | Aragaki | G06T 7/50 |
| 2019/0231296 A1* | 8/2019 | Jackson | A61B 6/488 |
| 2020/0304707 A1* | 9/2020 | Williams | G06N 3/088 |
| 2022/0165395 A1* | 5/2022 | Patil | G06F 11/3058 |

OTHER PUBLICATIONS

Sled, et al: "A Non-parametric Method for Automatic Correction of Intensity Non-uniformity in MRI Data", 1997.

* cited by examiner

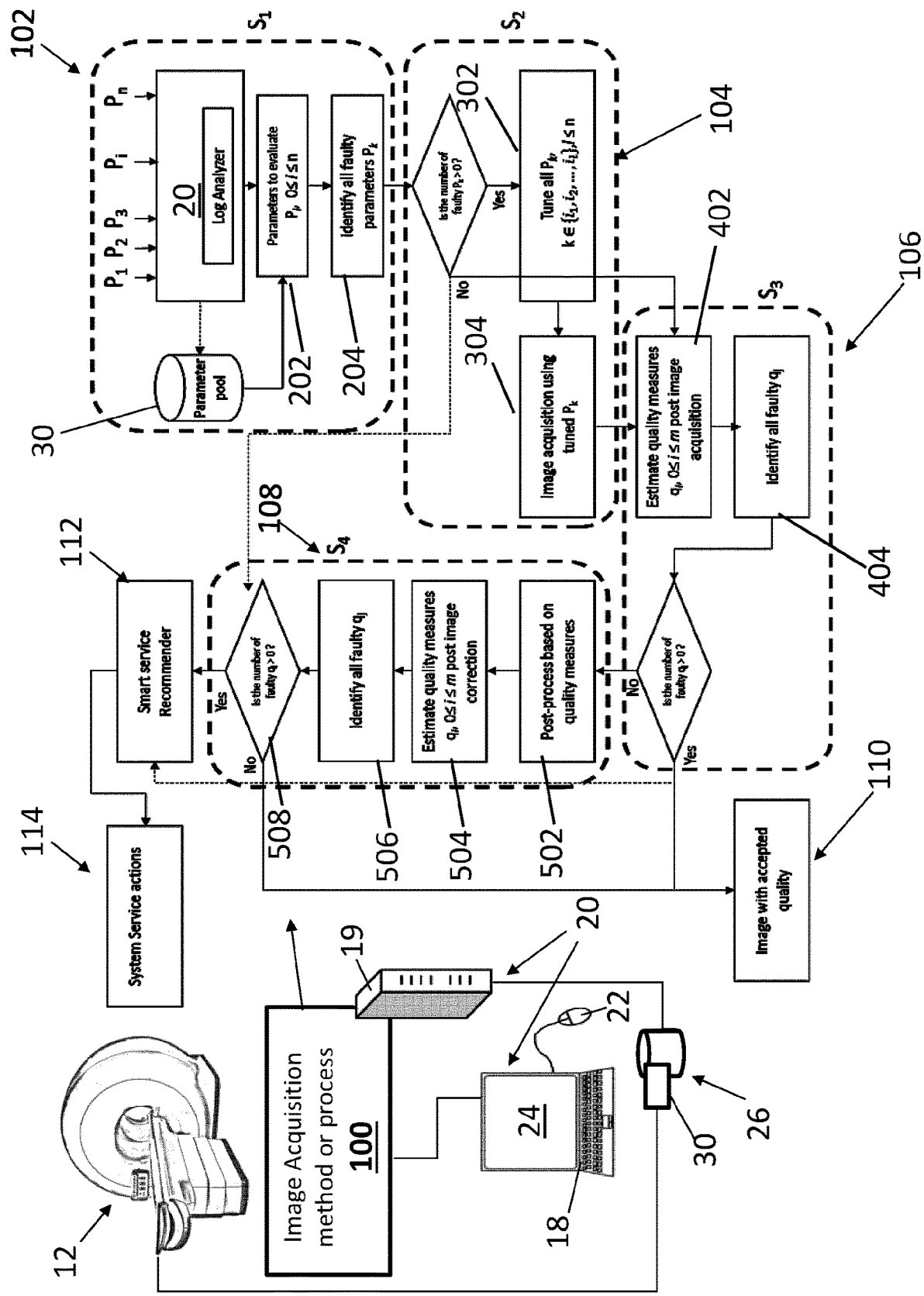

MEDICAL IMAGING SYSTEMS AND METHODS WITH AUTO-CORRECTION OF IMAGE QUALITY-BASED ON THE LOG ANALYSIS OF MEDICAL DEVICES

CROSS-REFERENCE TO PRIOR APPLICATIONS

This application is the U.S. National Phase application under 35 U.S.C. § 371 of International Application No. PCT/EP2020/060667, filed on Apr. 16, 2020, which claims the benefit of U.S. Provisional Patent Application No. 62/834,988, filed on Apr. 17, 2019. These applications are hereby incorporated by reference herein.

FIELD

The following relates generally to the imaging arts, medical imaging device optimization arts, medical imaging device auto-correction arts, and related arts.

BACKGROUND

Medical imaging is a crucial part of medical services which are critical for correct inference of many critical medical conditions. There are different imaging modalities that have specific purposes and are used for targeting different body parts (for example, X-ray for bones and magnetic resonance imaging (MRI) for soft tissue, etc.). A commonality among these diagnostic imaging modalities is the generation of a reconstructed image of a portion of a patient which is displayed on a display and that is used by clinicians for clinical analysis of the image for purposes such as clinical screening or diagnosis, assessment or monitoring of a medical condition, or so forth. Hence, the acquisition of the image with high image quality play a pivotal role in correct clinical assessment for the patient.

There are many factors which are involved in obtaining a reconstructed image and many techniques are used to render clinically useful image quality for the user. Among these factors, some are hardware-related, such as (by way of non-limiting examples): radiation detector pixel size (impacts image resolution); sensor characteristics such as sensitivity, linearity, detector uniformity across an array, and so forth (impacts diverse image quality metrics such as contrast and image uniformity); radiation source metrics such as brightness and beam shape (impacts image brightness and uniformity); magnetic field gradient uniformity in magnetic resonance imaging (MRI) scanners (impacts numerous image quality metrics); robotic patient support/transport hardware (where vibrations or other motion from such hardware can introduce blurring or motion artifacts in the image); and so forth. These various hardware components typically have detailed manufacturing specifications which the components are expected to meet at the time of installation. But over time, or due to physical conditions of the sensors used by the imaging modalities or the physical condition of the units housing the sensors or the various cables or any other related part or external environmental factors, image quality of the reconstructed images may degrade over time.

Many modern medical imaging devices are complex machines which are made up of many tens of thousands of components, systems, and sub-systems, and which have a high level of computerization including numerous installed sensors continuously monitoring performance of the various components, systems, and sub-systems. Servicing and maintenance of medical imaging systems is usually a mixture of preventative maintenance (e.g., replacing components on a fixed schedule), precautionary maintenance (e.g. replacing a component or sub-system whose performance is degrading as indicated by relevant sensors, although still functioning within an acceptable performance envelope and perhaps not yet recognized to be degrading image quality), and repairs of components or sub-systems that have failed or are no longer operating within the acceptable performance envelope (e.g. are producing clinically significant degradation of image quality). In many modern medical imaging devices, the sensor data are recorded in an ongoing machine log, and similarly maintenance or servicing performed on the imaging device is recorded in a servicing log. These logs are typically used in scheduling preventative or precautionary maintenance, and may also be referenced by a servicing technician to diagnose a device malfunction reported by the user of the imaging device. By way of such approaches, image quality degradation over time due to hardware degradation is identified and remediated.

The following discloses new and improved systems and methods to overcome these problems.

SUMMARY

In one disclosed aspect, a device for optimizing an image acquisition device includes at least one electronic processor operatively connected to read a machine log of the image acquisition device. A non-transitory computer readable medium stores instructions readable and executable by the at least one electronic processor to perform an image acquisition method. The method includes: extracting logged parameters of the image acquisition device from the machine log of the image acquisition device; identifying one or more out-of-range parameters of the image acquisition device from the logged parameters extracted from the machine log of the image acquisition device; automatically tuning one or more electrical or mechanical settings of the image acquisition device on the basis of the one or more out-of-range parameters to transform the image acquisition device into a tuned image acquisition device; and controlling the tuned image acquisition device to acquire one or more images of a patient.

In another disclosed aspect, a non-transitory computer readable medium stores instructions executable by at least one electronic processor to perform an image acquisition method. The method includes: computing one or more image quality metrics for one or more images acquired by an image acquisition device; identifying one or more out-of-range image quality metrics from the computed one or more image quality metrics; selecting one or more image filters on the basis of the one or more out-of-range image quality metrics; and applying the selected one or more image filters to the acquired one or more images to generate one or more improved images of a patient.

In another disclosed aspect, an image acquisition method includes: extracting logged parameters of an image acquisition device from a machine log of the image acquisition device; identifying one or more out-of-range parameters of the image acquisition device from the logged parameters extracted from the machine log of the image acquisition device; tuning one or more electrical or mechanical settings of the image acquisition device on the basis of the one or more out-of-range parameters to transform the image acquisition device into a tuned image acquisition device; controlling the tuned image acquisition device to acquire one or more images of a patient; computing one or more image quality metrics for the acquired one or more images; identifying one or more out-of-range image quality metrics from the computed one or more image quality metrics; selecting one or more image filters on the basis of the one or more out-of-range image quality metrics and on the further basis of the one or more out-of-range parameters of the image acquisition device; and applying the selected one or more image filters to the acquired one or more images to generate one or more improved images of a patient.

One advantage resides in identifying causes of imaging device degradation.

Another advantage resides in providing an improved medical imaging device which provides automatic tuning of hardware components of the imaging device.

Another advantage resides in providing automatic servicing recommendations such as recommending replacing components of an imaging device that are adversely impacting image quality, in which the replacement recommendations are delayed by the hardware tuning thereby extending useful service life of components.

Another advantage resides in extending the useful service life of components of an imaging device by acquiring images with image quality adjusted by post-acquisition image processing applied on the basis of a state of the component as automatically monitored in a machine log of the imaging device.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

FIG. 1 diagrammatically shows an illustrative device for optimizing an image acquisition device according to one aspect.

DETAILED DESCRIPTION

In some embodiments disclosed herein, machine log data are leveraged to tune imaging device hardware for improved image acquisition. In some such embodiments, an artificial intelligence (AI) system is trained to identify faulty machine parameters based on log data. The log patterns that serve as input to the AI may be handcrafted and/or machine learned log patterns. If a faulty machine parameter value is identified by the AI (e.g., a machine parameter value is identified by the AI as associated with significantly degraded image quality), then a machine learning (ML) model is used to adjust (i.e. tune) one or more hardware settings of the imaging device to improve the image. The image is then acquired (including any image reconstruction processing) using the tuned imaging device.

In some embodiments disclosed herein, image quality metrics are computed for the resulting image. These image quality metrics are input along with the image, and optionally also along with faulty machine parameter values identified by the AI, to an AI system trained to apply filter(s) or other post-acquisition image processing to improve the image.

In other embodiments disclosed herein, the ML system that performs the hardware tuning may also be trained to optimally identify service recommendations. For example, log patterns may be used to identify degradation of the X-ray tube in a CT scanner. Initially, this will be compensated by adjusting the X-ray tube operating parameters to maintain image quality. Secondarily, as the log patterns indicate progressively more degradation of the X-ray tube the ML may additionally output a recommendation to replace the X-ray tube within a certain timeframe. Advantageously, in such embodiments the recommendation to service or replace a hardware component may be delayed to the extent that the tuning ML can tune machine parameter(s) (and/or the post-acquisition image processing AI can post-process images) to compensate for degradation of the hardware component. This can extend the effective service life of the hardware component between replacements/servicing compared with a service recommender system that addresses degradation of hardware components only by recommending service or replacement.

Similarly, the AI system that performs the post-processing may issue servicing recommendations based on trained responses to the input image quality metrics.

In an illustrative example of operation of some embodiments disclosed herein, at an initial time (e.g., $T_0$), analysis of recorded log data of the imaging device by the AI does not record any parameters of the imaging device that are likely to be significantly degrading image quality, and the imaging device is acquiring and generating data without any artifacts. However, as time progresses (e.g., $T_1$), the AI detects parameters in log files that degrade image quality, and acquired image has artifacts or other degradation. The ML adjusts one or more hardware component parameters, thus tuning the hardware of the imaging device and correcting the subsequently acquired image. The ML may optionally also propose field corrective action(s) that needs to be carried out at site by equipment supplier (e.g., OEM) with specific input about which part of the imaging device is to be repaired or replaced.

With reference to FIG. 1, an illustrative device for optimizing an image acquisition device (also referred to as an imaging device) 12 is shown. The image acquisition device 12 can be a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 12 may also be a hybrid imaging device such as a PET/CT or SPECT/CT imaging system.

FIG. 1 also shows an electronic processor 20, typically a server computer 19 or a plurality of server computers, e.g. interconnected to form a server cluster, cloud computing resource, or so forth), although the electronic processor 20 may be alternatively or additionally embodied as a workstation computer 18, or more generally a computer. The illustrative workstation 18 comprises a computer or other electronic data processing device with typical components, such as at least one microprocessor, at least one user input device (e.g., a mouse, a keyboard, a trackball, and/or the like) 22, and a display device 24 (e.g. an LCD display, plasma display, cathode ray tube display, and/or so forth). In some embodiments, the display device 24 can be a separate component from the workstation 18. The workstation 18 may optionally operate as a user interface or controller for the medical imaging device 12.

The electronic processor 20 is operatively connected with one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage accessible by the server 19, an internal hard drive of the workstation 18, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors (e.g. the server 19 and processor of the workstation 18).

The non-transitory storage media 26 stores instructions executable by the at least one electronic processor 20. The instructions include instructions to identify problems with the image acquisition device 12 that dilutes image quality, and providing a recommendation to remedy the identified problems. In some additional/alternative embodiments, the instructions automatically implement the recommendation, e.g. by automatically tuning one or more settings of hardware of the imaging device 12. In addition, a machine log 30 is recorded for the imaging device 12 and stored on the non-transitory storage medium 26. The machine log 30 stores various information pertaining to operation of the medical imaging device 12. For example, the machine log 30 stores sensor readings acquired by sensors that monitor parameters of hardware of the imaging device 12. Such sensors may, for example, include (by way of non-limiting illustration): temperature sensors monitoring temperature of various components; electrical sensors monitoring electric current, voltage, resistance, or so forth at various points in electric circuitry of hardware components; flux and/or intensity sensors measuring optical light, electron beam energy, or other types of outputs; position sensors measuring positions of robotic hardware (rotating gantry, patient positioning system, et cetera); and so forth.

The machine log 30 may store information on imaging sessions, e.g. start/end times, imaging sequences executed by the imaging device 12, patient position (e.g. from robotic positioning system), X-ray tube operating parameters during a CT scan, and/or so forth. The machine log 30 may store imaging device calibration information, such as counts/locations of dead detector pixels, detector dark current readings, and/or so forth. The machine log 30 may store servicing information on servicing operations performed on the imaging device 12, such as timestamped service calls, service summaries entered by servicing technicians, and/or so forth. Again, these are merely non-limiting illustrative examples of some types of information that may be recorded in the machine log 30; the specific information that is logged is dependent upon the imaging modality, the specific make/model of imaging device, the configuration of the specific machine logging system, and other factors.

A substantial amount of logged information is automatically generated by sensors, imaging session control software, or the like, but some logged information may be manually entered (e.g. service summaries). Still further, it is to be appreciated that the machine log 30 may be logically divided into multiple logs, such as a sensor(s) log(s), a service log, and an imaging sessions log (again, by way of non-limiting illustrative example). As used herein, the machine log 30 is to be understood as broadly encompassing such a plurality of machine logs. The machine log 30 may be stored locally, e.g. in a database at the hospital where the imaging device 12 is located, and/or may be stored (e.g. backed up) at a remote location, e.g. at a server maintained by the manufacturer of the imaging device 12. The at least one electronic processor 20 is in operative communication with the image acquisition device 12, and is also in operative communication to read the machine log 30. Such operative communication with the machine log 30 may be direct, e.g. the illustrative server 19 may receive sensor data from the imaging device 12 and directly maintain the machine log 30, or indirect, e.g. the illustrative server 19 may download a most recent portion of the machine log 30 stored at the manufacturer's server.

The device 10 is configured as described above to perform an image acquisition method or process 100. The non-transitory storage medium 26 stores instructions which are readable and executable by the at least one electronic processor 20 (e.g. the workstation 18 and/or the server 19) to perform disclosed operations including performing the image acquisition method or process 100. In some examples, the method 100 may be performed at least in part by cloud processing.

With continuing reference to FIG. 1, an illustrative embodiment of the image acquisition method 100 is diagrammatically shown as a flowchart. At 102, log parameters of the image acquisition device 12 are analyzed to identify faulty parameters. (As used herein, a faulty parameter is one whose value is suspected, e.g. based on AI analysis as in illustrative embodiments disclosed herein, to be causing or contributing to a significant degradation in image quality). At 104, one or more electrical or mechanical settings of the imaging device 12 are tuned to compensate for the faulty parameter and an image is acquired with the tuned parameters. At 106, quality measures of the acquired image are analyzed to identify faulty quality measures. At 108, the image is post-processed and the quality measures of the acquired image are analyzed to identify faulty quality measures. At 110, an image with an accepted quality is acquired. Additionally or alternatively, at 112, a recommendation to correct for the faulty image quality measures is output, where a corresponding correction action can be performed at 114.

At 102, log parameters P stored in the machine log 30 of the image acquisition device 12 are extracted by the at least one electronic processor 20. The log parameters P indicate a current state of components of the image acquisition device 12. Some of these parameters may impact image quality metrics such as, for example, sharpness/blur, contrast, distortion, vignetting (e.g., reduction in brightness/saturation of image toward the periphery as compared to middle portion of the image), chromatic aberration, noise, change in dynamic range, and presence of a vertical or horizontal line (e.g., thick or thin). Degradation in one or more of the logged parameters may, directly or indirectly, lead to undesired artifacts or other degradation in the image (which may be quantifiable by one or more of the just-mentioned image quality metrics). To extract the parameters from the machine log 30, the type of modality of the image acquisition device 12 is identified, and relevant parameters are extracted (at 202) from the machine log 30 using, e.g., natural language processing (NLP). (In a variant embodiment, an instance of the method 100 is executed for a single imaging device, in which case the imaging modality may be known a priori and the instructions stored on the non-transitory storage medium 26 which are executed may be modality-specific in this case there is no need for a step of identifying the imaging modality). To identify a faulty parameter, these parameters can be analyzed statistically if the desired acceptable ranges are known in advance, e.g., from manuals or by using a supervised learning method. From a list of "n" parameters, the most suspect parameters can be identified in, for example, a random forest analysis. The identified lists of suspect parameters are candidates for tuning of the components of the image acquisition device 12. At 204, one or more out-of-range (i.e., faulty or suspect) parameters Pk of the image acquisition device 12 extracted from the machine log 30 of the image acquisition device are identified. The out-of-range parameters Pk can be identified by a ML model implemented on the at least one electronic processor 20. The ML model is trained on training data comprising sets of logged parameters labelled with image quality values for images acquired by the image acquisition device having the sets of logged parameters (e.g., stored in the machine log 30 and/or the non-transitory storage media 26).

With continuing reference to FIG. 1, operation 104 is described in more detail. At 302, one or more electrical or mechanical settings of the image acquisition device 12 are tuned on the basis of the one or more out-of-range parameters Pk to transform the image acquisition device into a tuned image acquisition device. In a typical imaging system, the source for the imaging generation could be, for example, an X-ray tube, or a magnet in the case of an MIll, or ultrasound transducers as in an ultrasound (US) machine. (These are non-limiting examples. Medical imaging devices of certain modalities may not have an imaging generation source for example, a PET scanner detects 511 keV gamma rays emitted by a radiopharmaceutical administered to the patient). Each of these sources have mechanical/electrical parameters which has an ability to affect the image quality based on tuning constraints. A correction factor is determined that is responsible for the correcting the image in case of degradation. Similarly, a radiation detector array of a CT scanner, PET scanner, SPECT camera, or the like has a range of logged parameters that can impact image quality, such as dark current levels for the pixels of the detector array, sensitivity calibration values for sensor pixels, and/or so forth. Settings that might be tuned to compensate for high dark current might, for example, include adjustment of a bias voltage on a detector pixel.

The tuning at operation 302 includes applying a tuning model (e.g., stored in the non-transitory computer readable media 26) to the one or more out-of-range parameters Pk to generate tuned values for the one or more electrical or mechanical settings of the image acquisition device 12. The one or more electrical or mechanical settings are adjusted to the tuned values generated by the tuning model. The tuning model comprises a machine learned tuning model trained on historical training data comprising sets of logged parameters (e.g., stored in the non-transitory storage media 26) labelled with image quality values (generated either automatically as image quality metrics and/or manually labeled by expert clinicians) for images acquired by the image acquisition device using the sets of logged parameters, with the images further labeled with the values of the electrical and/or mechanical settings of the imaging device 12 which are contemplated to be tuned by the ML tuning model. The training optimizes the ML to select tuned value(s) for electrical and/or mechanical settings of the imaging device 12 that yield the highest image quality labels in the historical training set for images with similar out-of-range parameters. In one example, this adjustment process is automatically performed by the at least one electronic processor 20. In another example, the tuned values generated by the tuning model can be displayed on the display device 24 for review and approval by a user before the adjustment process is performed by the at least one electronic processor 20. Although a ML tuning model is illustrated, the tuning model could be otherwise implemented, e.g. as an analytic function dependent on the one or more out-of-range parameters Pk.

The identification of the modality type is performed based on the log file analysis using NLP which provides the classification of the modality type. (As previously mentioned, in some embodiments the method 100 is modality-specific in which case the step of identifying the modality type is omitted). Based on the tuned values, the trained ML models search for parameters in the log file that are associated with the modality (e.g., for X-ray tube). Some non-limiting illustrative examples of mechanical/electrical settings of an X-ray tube that may be tuned by such an approach are set forth in Table 1.

TABLE 1

| | | | |
|---|---|---|---|
| Generator's max power | | 5 kW (Rotating anode) | 3.5 kW (fixing anode) |
| Frequency | | 40 kHz | 40 kHz |
| Fluoroscopy | Focus | 0.3 mm | 0.6 mm |
| | kV | 40~120 kV | 40~110 kV |
| | mA mA-L | 0.1~1.3 mA | 0.1~1 mA |
| | mA-II | 1~3 mA | 1~2.7 mA |
| Radiography | pulsing fluoroscopy (option) | 0.5, 1, 2, 3, 4, 5, 6 steps adjustable | 0.5, 1, 2, 3, 4, 5, 6 steps adjustable |
| | focus | 0.6 mA | 1.5 mA |
| | kV | 40~120 kV | 40~110 kV |
| | mA | 70~24 mA | 70~30 mA |
| Image system | S | 0.04~3.2 s | 0.1~3.2 s |
| | Image intensifier | 9" | 9" |
| | camera | CCD | CCD |
| | monitor size | 14" | 14" |
| | resolution | 14 LP/cm | 14 LP/cm |
| C-arm | height adjustment | 400 mm | 400 mm |
| | horizontal movement | 200 mm | 200 mm |
| | horizontal vibrating movement range | 10.5° | 10.5° |
| | | 180° | 180° |
| X-ray tube assembly | trail movement range | 115° | 115° |
| | X-ray tube | rotating anode | fixed anode |
| Collimator | Max thermal capacity | 200 KHU | 45 KHU |
| | X-ray collimator | iris electrical | iris electrical |
| Optional | Digital workstation, image acquiring card | | |

The extracted parameters Pk are fed to the trained ML models, which outputs tuned values for one or more electrical and/or mechanical settings of one or more components of the image acquisition device 12 (e.g., mechanical/electrical) so as to compensate for image degradation caused by the out-of-range parameter(s) Pk. In some embodiments, this is done automatically by the electronic processor 20 (e.g., if the electronic processor 20 includes or communicates with the workstation 18 serving as the controller for the imaging device 12). In some embodiments (or for certain adjustments to critical settings of the imaging device 12), the tuned value of a setting may instead be initially proposed to the user, for example by being displayed on the display 24 of the workstation 18 along with a user dialog via which the user may select (via the user input device 22) to accept or reject the tuning operation. In these latter embodiments, the setting is only adjusted to the tuned value if the user selects to accept the tuning operation. In any of these embodiments, the tuning operation is typically recorded in the machine log 30 in common with most significant events occurring in or to the imaging device 12.

Once the tuning process is complete, the tuned image acquisition device 12 is controlled by the at least one electronic processor 20 to acquire one or more images of a patient (e.g., at 304).

In some embodiments, the image acquisition method 100 can proceed directly to operation 112, in which a recommendation to correct for the faulty image quality measures is output. Operation 112 includes applying a service recommender model (e.g., stored in the non-transitory storage media 26) to the one or more out-of-range parameters Pk to generate service recommendations for the image acquisition device 12. The service recommender model comprises a machine learned model trained on training data comprising sets of logged parameters labelled with image quality values for images acquired by the image acquisition device 12 using the sets of logged parameters P. In some examples, the service recommender model is applied by the at least one electronic processor 20 to the one or more out-of-range parameters and to one or more image quality metrics generated for the acquired one or more images to generate the service recommendations for the image acquisition device 12. The service recommendations can be displayed on the display device 24. The recommendation to replace a component can be delayed by the tuning, which can effectively extend the useful service life while still scheduling timely replacement to avoid unnecessary shutdowns.

In some embodiments, the service recommendations can include a recommendation to order one or more replacement parts for the image acquisition device 12. For example, the recommendation as displayed on the display device 24 can include a link or button to allow the user to order the needed replacements parts (e.g., by linking the user with a third-party parts ordering service or with a company that manufactures the needed replacement parts). The user can also be able to enter shipping information (e.g., a shipping address, a delivery date, a priority shipping level, and so forth). In some examples, the parts order can include a priority and timing (e.g., if the part is needed immediately). In other examples, based on the tuning operation 302, the priority and timing of the ordered replacement parts based on which specific parameters are below the designated thresholds, a type of artifacts detected in the image, filters used to remedy artifacts in the images, and so forth. A service scheduler can be implemented in the workstation 18 or the server 19 to prioritize the orders based on a schedule service appointment, a service appointment of nearby imaging systems 12, and so forth.

In other embodiments, the image acquisition method 100 proceeds to operation 106. At 402, one or more image quality metrics are computed or estimated (e.g., by the at least one electronic processor 20) for the image(s) acquired at operation 304. The computed image quality metrics may include, by way of non-limiting illustrative examples, one or more of sharpness, blur, contrast, distortion, vignetting, chromatic aberration, noise, change in dynamic range, and/or presence of a vertical or horizontal line. At 404, one or more out-of-range image quality metrics are identified (e.g., by the at least one electronic processor 20) from the computed one or more image quality metrics.

At 108, the post-processing operations are performed. At 502, one or more image filters are selected on the basis of the one or more out-of-range image quality metrics, and are applied to the image to improve its image quality. In some embodiments, the one or more image filters are selected on the basis of the one or more out-of-range image quality metrics, and on the further basis of the one or more out-of-range parameters of the image acquisition device 12. The selection 502 may employ an AI algorithm trained on historical post-processed images labelled with pre-post-processing image quality metrics (and also with out-of-range parameters of the image acquisition device 12, for embodiments in which the post-processing operations are also selected on that basis). The training optimizes the AI to select the post-processing operation(s) that yield the highest improvement in image quality metrics going from the pre-processed to post-processed image in the historical training set for images with similar out-of-range parameters. Also, at 502, the selected one or more image filters are applied (e.g., by the at least one electronic processor 20) to the acquired one or more images (at 304) to generate one or more improved images of a patient (e.g., at operation 110). At an optional step 504, the image quality metrics are computed for the post-processed images, and checked at 506 to determine whether any image quality metrics are still faulty (e.g. out of an acceptable range). At 508, if any image quality metrics remain faulty then this is input to the recommender 112 to generate a servicing recommendation.

The ML models stored in the non-transitory storage media 26 can be, for example, Generative Adversarial Networks (GANs). The AI algorithms described above can be based on the models, along with Deep Learning models, GAN models, statistical models, and so forth. Inputs to these types of networks can include one or more corrupted images, along with list of parameters and correction algorithms. The ML models use these inputs to learn and generate appropriate correction techniques and recommendations.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A device for optimizing an image acquisition device, the device including:
    at least one electronic processor operatively connected to read a machine log of the image acquisition device; and
    a non-transitory computer readable medium storing instructions readable and executable by the at least one electronic processor to perform an image acquisition method including:
        computing one or more image quality metrics for one or more images acquired by an image acquisition device, wherein the computed one or more image quality metrics includes one or more of sharpness, blur, contrast, distortion, vignetting, chromatic aberration, change in dynamic range, and/or presence of a vertical or horizontal line;
        with a first machine learning model comprising a tuning model, identifying one or more out-of-range image quality metrics from the computed one or more image quality metrics;
        selecting one or more image filters on the basis of the one or more out-of-range image quality metrics;
        applying the selected one or more image filters to the acquired one or more images to generate one or more improved images of a patient;
        with a second machine learning model, extracting logged parameters of the image acquisition device from the machine log of the image acquisition device;
        identifying one or more out-of-range parameters of the image acquisition device from the logged parameters extracted from the machine log of the image acquisition device;
        automatically tuning one or more electrical or mechanical settings of the image acquisition device on the basis of the one or more out-of-range parameters to transform the image acquisition device into a tuned image acquisition device;

controlling the tuned image acquisition device to acquire one or more images of a patient using the automatically tuned one or more electrical or mechanical settings of the image acquisition device;

applying a service recommender model to the one or more out-of-range parameters to generate service recommendations for the image acquisition device; and displaying the service recommendations generated by the service recommender model on a display device, wherein the service recommender model comprises a machine learned model trained on training data comprising sets of logged parameters labeled with image quality values for images acquired by the image acquisition device using the sets of logged parameters, the service recommender model being a Generative Adversarial Network model.

2. The device of claim 1, wherein the tuning includes:

applying a tuning model to the one or more out-of-range parameters to generate tuned values for the one or more electrical or mechanical settings of the image acquisition device; and automatically adjusting the one or more electrical or mechanical settings to the tuned values generated by the tuning model, wherein the tuning model comprises a machine learned tuning model trained on training data comprising sets of logged parameters labeled with image quality values for images acquired by the image acquisition device using the sets of logged parameters.

3. The device of claim 1, wherein the identifying of the one or more out-of-range parameters includes:

identifying at least one out-of-range parameter by applying a machine learning model to data of the machine log;

wherein the machine learning model is trained on training data comprising sets of logged parameters labeled with image quality values for images acquired by the image acquisition device having the sets of logged parameters.

4. The device of claim 1, wherein the applying comprises:

applying the service recommender model to the one or more out-of-range parameters and to one or more image quality metrics generated for the acquired one or more images to generate the service recommendations for the image acquisition device.

5. The device of claim 1, wherein the selecting comprises:

selecting the one or more image filters on the basis of the one or more out-of-range image quality metrics and on the further basis of the one or more out-of-range parameters of the image acquisition device.

6. A medical imaging system comprising:

an image acquisition device, the image acquisition device being one of a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; or an ultrasound (US) image acquisition device;

a display; and a device as set forth in claim 1;

wherein the instructions stored on the non-transitory computer readable medium are further readable and executable by the at least one electronic processor to display, on the display, the one or more images of the patient acquired using the automatically tuned one or more electrical or mechanical settings of the image acquisition device.

7. A non-transitory computer readable medium storing instructions executable by at least one electronic processor to perform an image acquisition method for optimizing an image acquisition device, the method including:

computing one or more image quality metrics for one or more images acquired by an image acquisition device, wherein the computed one or more image quality metrics includes one or more of sharpness, blur, contrast, distortion, vignetting, chromatic aberration, change in dynamic range, and/or presence of a vertical or horizontal line;

with a first machine learning model comprising a tuning model, identifying one or more out-of-range image quality metrics from the computed one or more image quality metrics;

selecting one or more image filters on the basis of the one or more out-of-range image quality metrics;

applying the selected one or more image filters to the acquired one or more images to generate one or more improved images of a patient;

a second machine learning model, extracting logged parameters of the image acquisition device from the machine log of the image acquisition device;

identifying one or more out-of-range parameters of the image acquisition device from the logged parameters extracted from the machine log of the image acquisition device;

automatically tuning one or more electrical or mechanical settings of the image acquisition device on the basis of the one or more out-of-range parameters to transform the image acquisition device into a tuned image acquisition device; and controlling the tuned image acquisition device to acquire one or more images of a patient;

applying a service recommender model to the one or more out-of-range parameters to generate service recommendations for the image acquisition device; and displaying the service recommendations generated by the service recommender model on a display device, wherein the service recommender model comprises a machine learned model trained on training data comprising sets of logged parameters labeled with image quality values for images acquired by the image acquisition device using the sets of logged parameters, the service recommender model being a Generative Adversarial Network model.

8. The non-transitory computer readable medium of claim 7, wherein the selecting comprises:

selecting the one or more image filters on the basis of the one or more out-of-range image quality metrics and on the further basis of the one or more out-of-range parameters of the image acquisition device.

9. The non-transitory computer readable medium of claim 7, wherein the computed image quality metrics includes a plurality of sharpness, blur, contrast, distortion, vignetting, chromatic aberration, change in dynamic range, and/or presence of a vertical or horizontal line.

10. The non-transitory computer readable medium of claim 7, wherein the tuning includes:
- applying the tuning model to the one or more out-of-range parameters to generate tuned values for the one or more electrical or mechanical settings of the image acquisition device; and
- automatically adjusting the one or more electrical or mechanical settings to the tuned values generated by the tuning model,
- wherein the tuning model comprises a machine learned tuning model trained on training data comprising sets of logged parameters labeled with image quality values for images acquired by the image acquisition device using the sets of logged parameters.

11. The non-transitory computer readable medium of claim 7, wherein the identifying of the one or more out-of-range parameters includes:
- identifying at least one out-of-range parameter by applying the second machine learning model to data of the machine log;
- wherein the machine learning model is trained on training data comprising sets of logged parameters labeled with image quality values for images acquired by the image acquisition device having the sets of logged parameters.

12. The non-transitory computer readable medium of claim 7, wherein the applying comprises:
- applying the service recommender model to the one or more out-of-range parameters and to one or more image quality metrics generated for the acquired one or more images to generate the service recommendations for the image acquisition device;
- wherein the service recommendations include ordering one or more replacement parts for the image acquisition device based on the one or more out-of-range parameters.

* * * * *